(12) United States Patent
Bertholdt

(10) Patent No.: US 8,444,700 B2
(45) Date of Patent: May 21, 2013

(54) MEDICAL IMPLANT AND PROCESS FOR THE PRODUCTION THEREOF

(75) Inventor: Günter Bertholdt, Heiningen (DE)

(73) Assignee: Bioregeneration GmbH, Garching (DE)

( * ) Notice: Subject to any disclaimer, the term of this patent is extended or adjusted under 35 U.S.C. 154(b) by 590 days.

(21) Appl. No.: 12/526,767

(22) PCT Filed: Feb. 12, 2008

(86) PCT No.: PCT/EP2008/051694
§ 371 (c)(1),
(2), (4) Date: Oct. 9, 2009

(87) PCT Pub. No.: WO2008/098944
PCT Pub. Date: Aug. 21, 2008

(65) Prior Publication Data
US 2010/0121431 A1    May 13, 2010

(30) Foreign Application Priority Data

Feb. 12, 2007    (DE) .......................... 10 2007 006 844

(51) Int. Cl.
*A61F 2/04* (2006.01)
(52) U.S. Cl.
USPC ..................... 623/23.68; 623/23.71; 623/1.24
(58) Field of Classification Search
USPC ........... 623/1.24, 1.26, 1.38, 1.41, 1.44–1.48, 623/1.49, 2.1, 2.12–2.19, 2.42, 23.64–23.76; 435/823; 428/35.7, 36.9, 36.92
See application file for complete search history.

(56) References Cited

U.S. PATENT DOCUMENTS

| 15,192 | A | 6/1856 | Peale |
| 6,800,753 | B2 * | 10/2004 | Kumar ............................. 536/57 |
| 7,709,631 | B2 * | 5/2010 | Harris et al. .................... 536/57 |
| 8,017,396 | B2 * | 9/2011 | Kumar ........................... 435/402 |
| 2003/0013163 | A1 | 1/2003 | Klemm et al. |
| 2004/0117004 | A1 * | 6/2004 | Osborne et al. ............... 623/1.36 |
| 2005/0037082 | A1 * | 2/2005 | Wan et al. ...................... 424/488 |
| 2010/0042197 | A1 * | 2/2010 | Bodin et al. ................... 623/1.1 |

FOREIGN PATENT DOCUMENTS

| DE | 3820574 | 12/1989 |
| DE | 102005011930 | 9/2006 |
| DE | 102006007412 | 8/2007 |

(Continued)

OTHER PUBLICATIONS

Klemm, D. et al. 2001. Bacterial synthesized cellulose—artificial blood vessels for microsurgery. Progress in Polymer Science, vol. 26, pp. 1561-1603.
International Search Report of the International Searching Authority for PCT/EP2008/051694 mailed Apr. 25, 2008 (3 pgs.).

*Primary Examiner* — David Isabella
*Assistant Examiner* — Suba Ganesan
(74) *Attorney, Agent, or Firm* — Harris Beach PLLC

(57) ABSTRACT

An elongate hollow body (1) comprising crystalline cellulose has on an inside wall a plurality of protuberances (3, 4) which extend into a lumen of the hollow body (1). A process for the production of an elongate hollow body (1) comprising crystalline cellulose comprises the steps: preparation of a hollow mold (12); cultivation of cellulose-forming organisms in an interior space formed by the hollow mold (12), in order to allow the hollow body (1) to grow in the interior space; demolding of the hollow mold (12). In the step of demolding the hollow mold (12), at least part of the hollow mold (12) is irreversibly deformed.

6 Claims, 4 Drawing Sheets

FOREIGN PATENT DOCUMENTS

| | | |
|---|---|---|
| EP | 0396344 | 11/1990 |
| WO | WO-9741803 A1 | 11/1997 |
| WO | WO-0161026 | 8/2001 |
| WO | WO-2004045458 | 6/2004 |
| WO | WO-2005011534 A1 | 2/2005 |
| WO | WO-2007016165 | 2/2007 |
| WO | WO-2007093445 | 8/2007 |

* cited by examiner

MEDICAL IMPLANT AND PROCESS FOR THE PRODUCTION THEREOF

BACKGROUND OF THE INVENTION

The invention relates to an elongate hollow body comprising crystalline cellulose according to the precharacterising clause of claim 1, and to a use of crystalline cellulose. It additionally relates to a process for the production of an elongate hollow body comprising crystalline cellulose, to an elongate hollow body produced by that process, and to a hollow mould for the production of the elongate hollow body.

PRIOR ART

In humans and in many mammals, the leg veins, which carry blood in the direction of the heart, are the blood vessels that are put under the greatest pressure by gravity. They have so-called vein flaps, that is to say protuberances in the blood vessel wall, which can act like a valve and ideally allow blood to flow only in a direction against gravity, while they prevent the blood from flowing back. As a result of a predominantly sedentary lifestyle and frequent standing, widening of the veins, so-called varicose veins, can occur with age, and the vein valves are then no longer able to fulfil their function. Congestion can occur and in severe cases ulcerations can form, and there may be a risk of losing the legs.

Arteries, especially those having a large inside diameter, can be replaced by synthetically produced tubes, for example of polyester ("Dacron") or expanded polytetrafluoroethylene (ePTFE, "Teflon®"). No replacement has hitherto been described for veins that carry blood to the heart. One reason may be that the blood flows more slowly in the veins, and the risk of an occlusion forming is therefore considerably higher than in the arteries. As therapy there are known elastic support stockings, which compress the veins and are thereby said to improve the function of the valves.

International Offenlegungsschrift WO 01/61026 A1 describes the production of a short hollow body having a small inside diameter from microcrystalline cellulose with the aid of bacteria. This hollow body is said to have proved to be functional over a prolonged period as an intraponate in the carotid artery of a rat and is said to have become populated by endothelial cells during that time despite a high flow velocity of the blood. In addition, the document reports that no foreign body reactions of any kind were observed.

PROBLEM UNDERLYING THE INVENTION

The object underlying the invention is to provide an improved elongate hollow body comprising crystalline cellulose. It is an additional object of the invention to provide a novel use of crystalline cellulose. It is a further object of the invention to provide an improved process for the production of an elongate hollow body comprising crystalline cellulose, and an improved hollow mould for the production of the elongate hollow body.

SOLUTION ACCORDING TO THE INVENTION

In order to achieve the object, the invention teaches elongate hollow bodies, comprising crystalline cellulose, having the features of claims 1 and 16, a use of an elongate cellulose hollow body having the features of claim 7, a process for the production of an elongate cellulose hollow body having the features of claim 8, and a hollow mould for the production of the elongate cellulose hollow body having the features of claim 17.

It is an aspect of the present invention that it uses the advantageous properties of crystalline cellulose, preferably microcrystalline cellulose in the natural form, as produced by the bacterium *Acetobacter xylinum*, to produce the elongate hollow body. Crystalline cellulose has been found to be particularly tissue-friendly in experiments.

It is an achievable advantage of the elongate hollow body according to the invention that its protuberances make it possible to control the flow of a medium, for example a blood flow, through the hollow body.

It is an achievable advantage of the elongate hollow body according to the invention that it can be populated with endothelial cells in order to prevent premature occlusion.

In particular, it is possible to populate it with endothelial cells before it is implanted.

It is an aspect of the process according to the invention for the production of a hollow body comprising crystalline cellulose that the Cellulose-forming organisms are enclosed in an interior space formed by a hollow mould, which interior space has the shape of the elongate hollow body and is filled with crystalline cellulose by the organisms.

It is an aspect of the process according to the invention that it makes use of the "broken mould" principle, that is to say uses a mould which loses its shape at least partially in the demoulding step.

It is an achievable advantage of the process according to the invention that undercuts formed by the protuberances do not constitute an obstacle during demoulding. In particular, it is possible for the protuberances not to be damaged or destroyed on demoulding.

The elongate hollow body according to the invention can be used, for example, as a replacement for a venous blood vessel in mammals, especially in humans.

COMPOSITION AND FURTHER DEVELOPMENT OF THE SOLUTION ACCORDING TO THE INVENTION

In a preferred embodiment of the invention, the elongate hollow body consists substantially of water and crystalline cellulose, particularly preferably microcrystalline cellulose, as is formed by the bacterium *Acetobacter xylinum*. The preferred material comprises less than 10 percent crystalline cellulose. In the preferred material, the water is bonded partially and with varying degrees of strength to the microcrystalline cellulose.

The elongate hollow body is preferably tubular, particularly preferably with openings at its ends, so that a medium, preferably a liquid medium, particularly preferably blood, can be conveyed through the lumen of the hollow body. Preferably, the lumen of the hollow body, particularly preferably also the outside, has a substantially circular cross-section. In an embodiment of the invention, the hollow body can have branches.

The protuberances of the elongate hollow body are preferably in such a form that they are able to slow down the flow of a medium that is conveyed through the elongate hollow body to a greater extent in a shut-off direction than in a direction contrary to the shut-off direction. The medium is conveyed through the elongate hollow body preferably in the longitudinal direction thereof. The preferred medium is a liquid medium, particularly preferably blood. The protuberances are preferably movable and/or deformable by the flow of the medium conveyed through the elongate hollow body. They are preferably in such a form that, when medium flows towards them in the shut-off direction, they increase their flow resistance, preferably by increasing their flow cross-section, preferably by moving into the medium.

In a preferred embodiment of the invention, the protuberances are in such a form that they can substantially suppress the flow of the medium in the shut-off direction, so that the medium is able to flow through the elongate hollow body substantially only contrary to the shut-off direction. As a result, it is possible for the function of the protuberances to correspond substantially to that of vein valves in human leg veins. This embodiment of the invention can therefore be particularly suitable as a replacement for leg veins in humans.

In a preferred embodiment, the protuberances are in the form of pockets; particularly preferably, they form the pockets together with the inside wall. Preferred pockets have a form similar to that of natural vein valves. The pockets are preferably each equipped with an opening, the openings of the plurality of pockets particularly preferably pointing substantially to the same end of the elongate hollow body. As a result, it is possible for all the pockets to have a uniform braking or non-braking action for a given flow direction.

Particularly preferably, a plurality of protuberances are located opposite one another in the lumen of the hollow body at the same height with respect to the longitudinal direction of the hollow body. Particularly preferably, precisely two protuberances are located opposite one another, but embodiments of the invention in which three or more protuberances are located opposite one another are also conceivable. The protuberances located opposite one another at the same height are preferably arranged at equal intervals with respect to a circumferential line of the hollow body. The protuberances located opposite one another are preferably so movable and/or deformable by a flow of a medium in the shut-off direction that they substantially close off the cross-section of the lumen, preferably by abutting one another, in order substantially to suppress the flow of the medium in the shut-off direction. On the other hand, they are so movable and/or deformable by a flow of a medium contrary to the shut-off direction that they form an opening between them in the cross-section of the lumen, so as to permit the flow of the medium contrary to the shut-off direction.

In the production process according to the invention, the direction of growth of the crystalline cellulose preferably extends substantially from a first longitudinal side of the interior space to its substantially opposite second longitudinal side. Because the cellulose hollow body does not grow along the longitudinal axis of the interior space but substantially perpendicular thereto, it is possible for the hollow body no longer to be limited in terms of its length by the layer height that can be achieved in the direction of growth. The layer height of cellulose layers that can be produced using known suitable bacteria is generally limited to about 20 mm.

In the production process according to the invention, the irreversible deformation can take place, for example, by plastic deformation, by a loss of form by breakage or by at least partial transition into a liquid or gaseous state of aggregation, preferably by melting or evaporation. However, embodiments of the invention are also conceivable in which deformation is effected by chemical treatment, for example by means of a solvent, or by mechanical treatment; for example by ultrasound. The part of the hollow mould that is irreversibly deformed in the demoulding step is preferably adjacent, before the deformation, to the cellulose formed in the hollow mould.

The hollow mould preferably comprises an outer mould and at least one mould core. The mould core preferably serves as a place marker for the lumen of the hollow body according to the invention. Preferably at least part of the mould core is deformed in the demoulding step. The outer mould is preferably tubular and particularly preferably has an opening or openings, for example longitudinal through-slots, on two opposing longitudinal sides. The preferred material for the outer mould is glass or another material that is chemically inert with respect to the substances and organisms used to carry out the process and/or formed therein.

Another possible outer mould consists of a gas-permeable material which is particularly preferably permeable to oxygen, for example silicone or a water-containing gel (hydrogel).

The preferred mould core has substantially the outer shape of an elongate cylinder, which is provided with indentations in order to form protuberances on the inside wall of the hollow body. The indentations are preferably slits. They preferably lie in a plane which encloses an angle of less than 90° (based on a complete angle of 360°), preferably from 15° to 75°, particularly preferably, from 30° to 60°, particularly preferably about 45°, with the longitudinal axis of the mould core. The indentations each extend preferably from the edge almost to the longitudinal axis of the mould core. Such a mould core makes it possible to form an elongate hollow body having pocket-like protuberances. The indentations preferably extend over the entire width of the mould core. In a preferred embodiment of the invention, the indentations are located opposite one another in pairs, in order to form a substantially arrow-like arrangement. In this manner it is possible to form protuberances in the form of pockets which are located opposite one another in pairs, the openings of which point in the same direction along the longitudinal axis of the elongate hollow body.

During demoulding, preferably the part of the hollow mould that is deformed, particularly preferably the entire mould, is treated with heat. The demoulding step preferably comprises at least partially melting the part of the hollow mould that is deformed. A preferred mould core comprises a stabilising element which extends substantially over the entire length of the mould core and which does not melt in the demoulding step. The stabilising element is preferably a leaf having a thickness of preferably less than 1 mm, particularly preferably from 0.02 to 0.1 mm. The stabilising element preferably lies in a common plane with the centre line of the mould core. The preferred stabilising element extends substantially over the entire width of the mould core. Preferred materials for the stabilising element are steel, plastics, carbon fibre or glass fibre materials.

In the demoulding step, the mould core is removed preferably substantially, particularly preferably quantitatively, that is to say without a residue. To that end, the mould core is preferably first heated in order to melt it. The stabilising element that is left behind is then removed from the hollow body. In a preferred embodiment of the invention, the melting point of the part of the hollow mould that melts in the demoulding step is above 28° C., particularly preferably at or above 30° C., particularly preferably at or above 60° C. It is an achievable advantage of this embodiment of the invention that the mould core remains stable during the cultivation of the cellulose. In a preferred embodiment of the invention, the melting point of the part of the hollow mould that melts in the demoulding step is below 100° C., particularly preferably below 80° C., particularly preferably 62° C. It is an achievable advantage of this embodiment of the invention that the mould core can be melted at a temperature at which the cellulose hollow body is not damaged.

The part of the mould core that melts during demoulding is preferably substantially hydrophobic. It is an aspect of this embodiment of the invention that use is made of the fact that a hydrophobic material is repelled by the hydrophilic surface of the cellulose hollow body. It is an achievable advantage of this embodiment of the invention that the hollow mould can be removed substantially quantitatively.

In a preferred embodiment of the invention, the part of the mould core that melts during demoulding comprises a thermoplastic material, particularly preferably a thermoplastic wax and/or polymer material. It is an achievable advantage of mould cores of thermoplastic materials that they can be produced by casting. It is a further advantage of wax and/or polymer materials that their surfaces can be smoothed simply by polishing, in order to facilitate the close attachment of the cellulose.

A preferred wax and/or polymer material comprises polyvinyl alcohol (PVA), particularly preferably in an amount of more than 1%, particularly preferably more than 50%. In a particularly preferred embodiment of the invention, the wax and/or polymer material consists substantially completely of polyvinyl alcohol. It is an achievable advantage of this embodiment of the invention that it is possible to avoid leaving behind toxic residues after removal of the hollow mould, because polyvinyl alcohol is non-toxic.

Another preferred wax and/or polymer material is so-called "summer wax", which is known from dentistry. It is an achievable advantage of this embodiment of the invention that the material is so mechanically stable that even filigree structures are retained. It is an achievable advantage of this embodiment of the invention that it is possible to avoid leaving behind toxic residues after removal of the hollow mould, because summer wax is non-toxic.

In a preferred production process according to the invention, the cellulose-forming organisms are bacteria, particularly preferably bacteria of the strain *Acetobacter xylinum*. It is conceivable for other cellulose-forming microorganisms also to be used, such as, for example, suitable strains of *Agrobacterium, Rhizobium, Sarcina, Pseudomonas, Achromobacter, Aerobacter* and *Zooglea*. Because the genes of the cellulose-synthesising enzyme complexes of *Acetobacter xylinum* are known, they could also be introduced into other microorganisms, such as, for example, *Escherichia coli*, using known molecular-biological processes, as a result of which these organisms could also synthesise cellulose.

Various nutrient media are described for the cultivation of *Acetobacter xylinum*. A suitable medium that is frequently used is Schramm and Hestrin's medium, which is described in Biochemical Journal 58 of 1954, pages 345-352. The totality of the relevant content of the above-mentioned article is incorporated by reference in the present disclosure. A disadvantage of this medium may be that it is not precisely defined, because it contains yeast extract and peptone.

A fully synthetic medium is preferred for carrying out the present invention, as described, for example, by Forng et al. in Applied and Environmental Biology of 1989, Vol. 55, No. 5, pages 1317-1319. The totality of the relevant content of the above-mentioned article is incorporated by reference in the present disclosure. A disadvantage of this medium may be slightly slower growth of the bacteria.

It is also conceivable to use so-called Kombucha mushroom tea for carrying out the invention. As well as comprising *Acetobacter xylinum*, this culture comprises many other organisms living in symbiosis, such as yeasts and bacteria, and can be supported by a medium consisting solely of black tea and sucrose (100 g/l).

For carrying out the process according to the invention, first a nutrient solution is preferably inoculated with the cellulose-forming organism outside the hollow mould. The cellulose is preferably microbial cellulose. The cellulose produced, for example, by the bacterium *Acetobacter xylinum* is initially less dense and less solid. It is therefore preferred to wait until a sufficiently dense layer of cellulose has been deposited on the nutrient medium. This is generally the case after about 7 to 10 days.

In a preferred embodiment of the invention, the hollow mould is laid horizontally with the lateral opening(s) on a growing layer of cellulose-producing bacteria. Because the specific gravity of the cellulose is approximately equal to that of the nutrient medium, the cellulose layer is preferably supported, for example by a net-like object of Teflon or glass.

The hollow body preferably grows in a direction perpendicular to the longitudinal axis of the interior space, particularly preferably from bottom to top. In a preferred embodiment of the invention, the bacteria pass into the hollow mould through one or more bottom opening(s) in the hollow mould in order to fill it completely with cellulose, it being possible at the same time for liquid medium to diffuse over a short path in order to supply the bacteria at the cellulose surface.

BRIEF DESCRIPTION OF THE DRAWINGS

The invention is explained in further detail hereinbelow with reference to diagrammatic drawings and an embodiment.

In the drawings.

DESCRIPTION WITH REFERENCE TO AN EMBODIMENT

Figure 1:
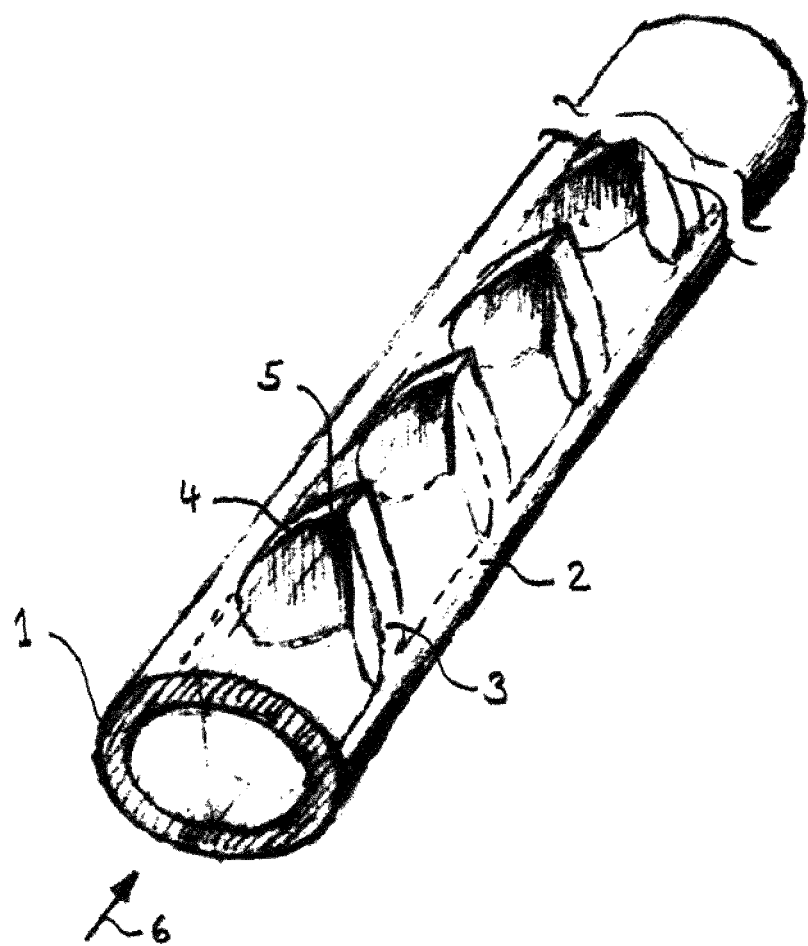
FIG. 1: shows a perspective vertical section, in diagrammatic form, of an elongate cellulose hollow body with protuberances on its inside wall.
Figure 2:
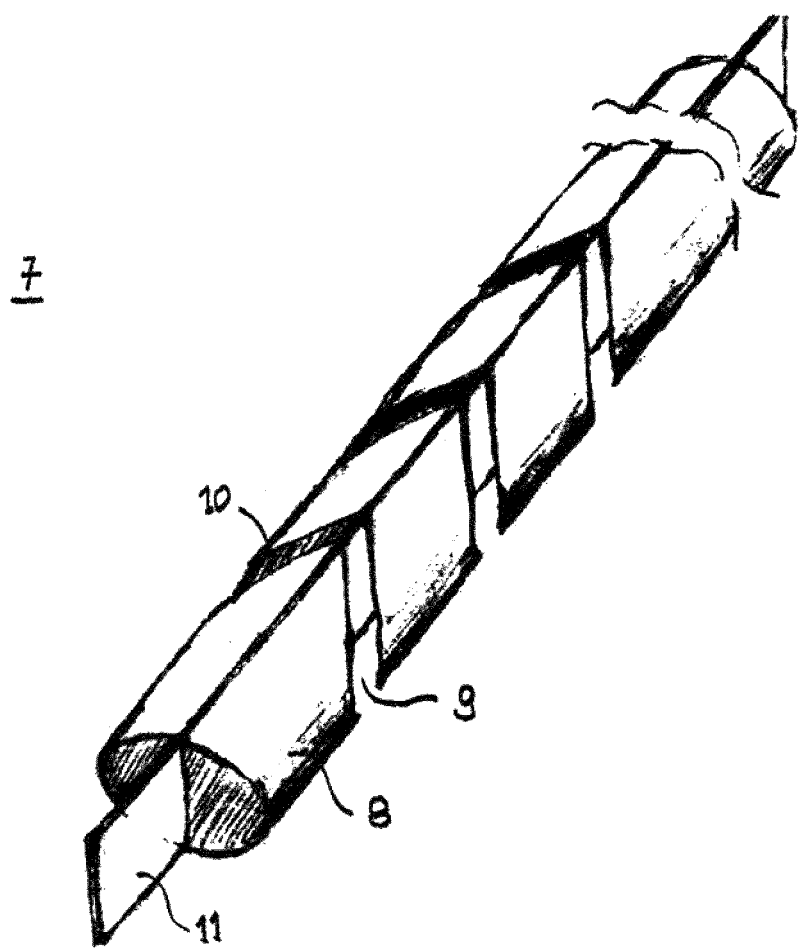
FIG. 2: shows a perspective view, in diagrammatic form, of a mould core for the process according to the invention for the production of an elongate cellulose hollow body, from above.
Figure 3:
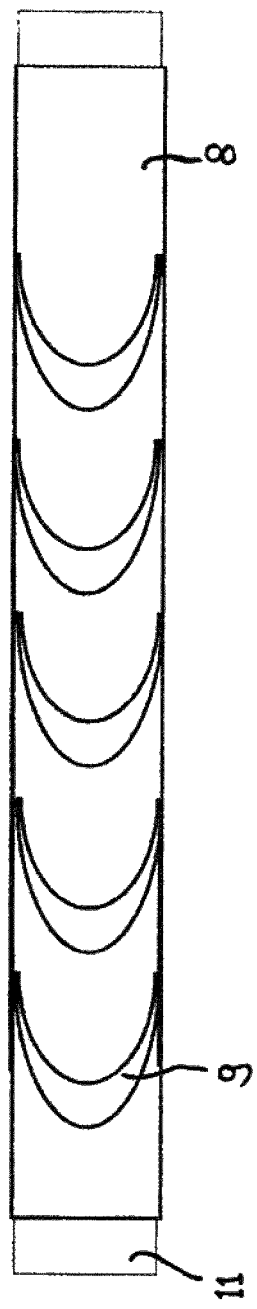
FIG. 3: shows a view, in diagrammatic form, of the mould core of FIG. 2, from above, wherein the stabilising element is located in the plane of the side.
Figure 4:
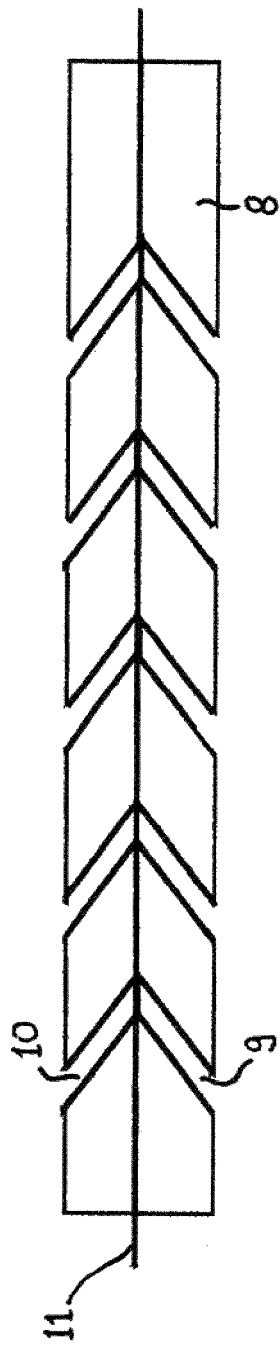
FIG. 4: shows a view, in diagrammatic form, of the mould core of FIGS. 2 and 3 from the side, wherein the stabilising element extends perpendicularly to the plane of the side.
Figure 5:
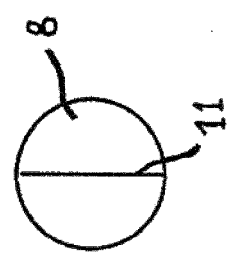
FIG. 5: shows a view, in diagrammatic form, of the mould core of FIGS. 2, 3 and 4 from the front, wherein the stabilising element extends perpendicularly to the plane of the side.

The elongate cellulose hollow body 1 shown in FIG. 1 is substantially tubular and has an outside diameter of about 3 mm. It is provided with protuberances 3, 4 which are arranged in pairs on its inside wall 2 and which form pockets with the wall 2 of the hollow body. The pairs of protuberances 3, 4 are each separated from one another by a narrow slit 5. When a medium, for example blood, flows towards the protuberances 3, 4 in the flow-through direction, they move in the direction towards the inside wall 2 and thereby increase the cross-section of the slit 5, so that the medium is able to pass. If, on the other hand, medium flows towards the protuberances 3, 4 contrary to the flow-through direction 6, that is to say in the shut-off direction, the protuberances 3, 4 are pressed against one another so that the slit 5 is closed. In this manner medium can largely be prevented from flowing through. The protuberances 3, 4 thus act like natural vein valves.

FIGS. 2 to 5 show a mould core 7 for the production of the cellulose hollow body shown in FIG. 1. The mould core 7 consists substantially of a wax cylinder 8 which is provided at regular intervals with pairs of slits 9, 10, which converge in a centre plane of the mould core in the manner of arrows. For stabilising the mould core 7, a spring steel leaf 11 is enclosed in the mould core 7 in that centre plane. The slits 9, 10 extend over the entire width of the wax cylinder 8 and as far as the steel leaf 11.

The production of the wax cylinder 8 which contains the spring steel leaf 11 is not simple in so far as the spring steel leaf 11 must be positioned exactly in the centre and it is difficult to fill a long tube having an inside diameter of several millimetres with hot wax without the formation of air bubbles and then demould it without destroying it. The mould core 7 is therefore produced using two halves of a glass tube which has been cut lengthwise, the two halves having been provided with a ground section so that they fit one another exactly. A flat sheet of Teflon is provided with a channel such that a glass tube half fits exactly therein in terms of its outside cross-section and the ground faces are flush with the Teflon sheet. The channel is slightly longer than the glass tube half and overlaps by about 1 cm at both ends. The Teflon sheet with the tube half inserted is heated to 90 to 100° C. in a hot cabinet and then filled with hot wax so that the wax is likewise flush with the ground glass section and the Teflon sheet. This procedure is repeated with the second glass half, with the difference that a thin spring steel leaf, whose width is slightly smaller than the inside diameter of the glass tube, is this time positioned over the half glass tube precisely in the middle. After cooling, the two glass halves filled with wax are joined together and heated at 90 to 100° C. again for a short time in the compressed state. After cooling again, the wax cylinder 8 with the embedded spring steel leaf 11 can be withdrawn by removing the glass halves.

The slits 9, 10 are then introduced with the aid of a hot wire on both sides and along the longitudinal axis of the wax cylinder 8 at intervals of about 5 cm. The slits 9, 10 extend from the outside to the spring steel leaf 11 and extend over the entire width of the wax cylinder 8. The object 7 formed thereby is so stable that it can be used as a place marker for the lumen of the cellulose hollow body 1.

Figure 6:
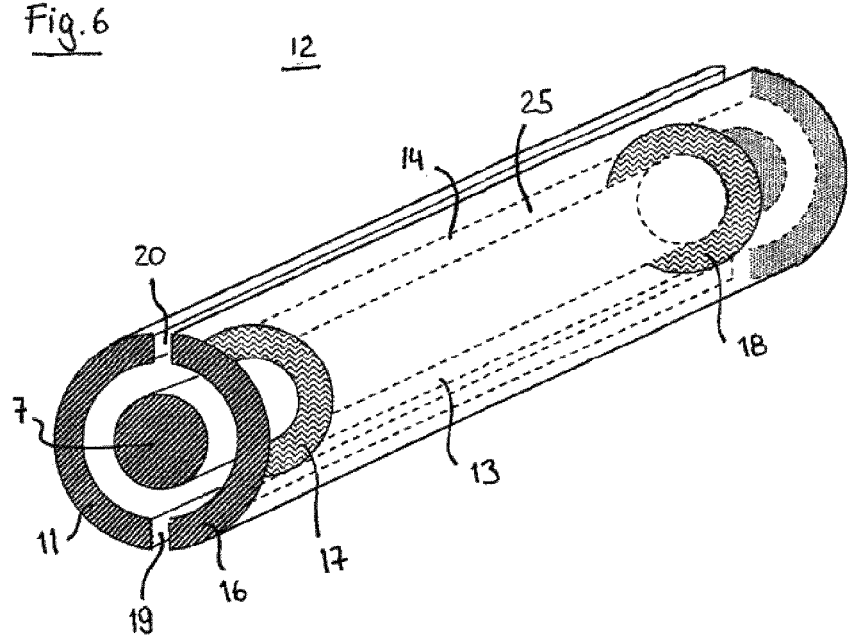
FIG. 6: shows a perspective view, in diagrammatic form, of a hollow mould having an outer mould and a mould core for carrying out the production process according to the invention.

As is shown in FIG. 6, the hollow mould 12 additionally has an outer mould with an interior space in the form of a hollow cylinder having two annular ends and longitudinal sides 13 and 14. The interior space is formed by two tube halves of glass 15, 16, the mould core 7 and two O-rings 13, 14. Slot-like openings 19, 20, which extend between the tube halves over the entire length of the hollow mould, make the interior space 25 of the hollow mould 12 accessible from the outside.

Figure 7:
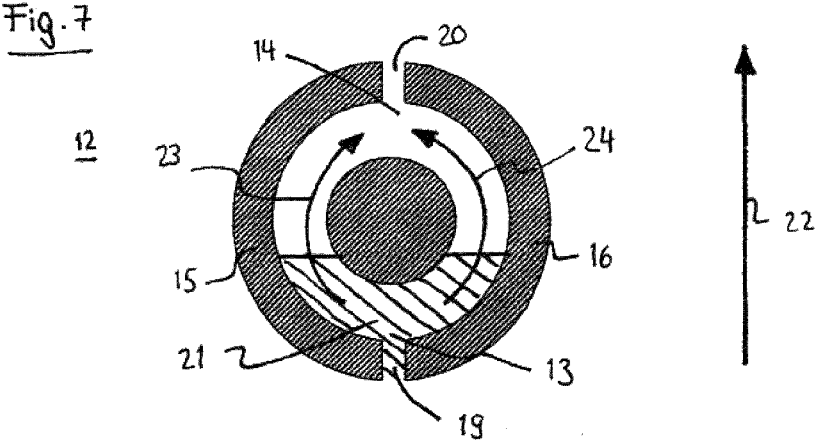
FIG. 7: shows a cross-sectional view, in diagrammatic form, of the hollow mould of FIG. 6 having an elongate hollow body which is not yet fully grown, showing the direction of growth.

As is shown in FIG. 7, the cellulose hollow body 21 grows inside the interior space 25 of the hollow mould 12 in the general direction indicated by the arrow 22, perpendicular to the longitudinal axis of the interior space, from one longitudinal side 13 to the other longitudinal side 14.

More precisely, the cellulose first grows into the hollow mould 12 through the opening 19 in the hollow mould 12 on the first longitudinal side 13 and then along the arrows 23, 24 to the other longitudinal side 14. At the same time, an exchange of air with the surroundings of the hollow mould 12 can take place by way of a second opening 20, in particular in order to supply oxygen to the organisms. Through the opening 19, the cellulose can transport the necessary nutrients from the outside from the growth medium to the organisms inside the hollow mould. Finally, the cellulose grows into the opening 20.

Figure 8:
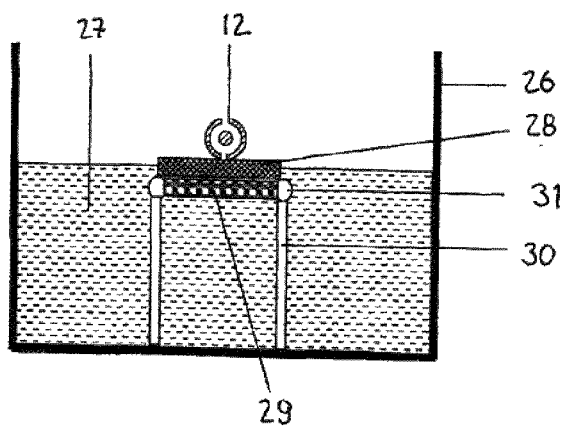
FIG. 8: shows a view, in diagrammatic form, of an arrangement for carrying out the production process according to the invention.

As is shown in diagrammatic form in FIG. 8, a sterile vessel 26 having a capacity of 2000 ml is filled with 1000 ml of a sterile nutrient solution 27 consisting of 20 g of glucose, 5 g of yeast extract, 5 g of bactopeptone, 2.7 g of sodium phosphate and 1.15 g of citric acid monohydrate, pH 6.0, and inoculated with a 3-day-old preliminary culture of *Acetobacter xylinum* (e.g. *Gluconacetobacter xylinum*, DSN No. 2325, DSZN Brunswick). When, after about 7 days, a layer 28 of cellulose having a thickness of about 3 mm has formed on the surface of the liquid, the layer 28 is supported by a net 29 of Teflon, expanded polytetrafluoroethylene (ePTFE), e.g. GLIDE dental floss, W.L. GORE & ASSOCIATES Inc., which is clamped in a glass frame 31 carried by glass supports 30. Two glass tubes (Duran glass), inside diameter 6 mm, wall thickness 1.5 mm, length 150 mm, are cut lengthwise so as to form two parts 15, 16 which, when the cut faces are put together, give a height of about 7 mm. The two glass tube parts 15, 16 are then positioned symmetrically around the mould core 7, which is equipped at each end with an O-ring 17, 18 of rubber (vulcanised rubber), and secured at the ends with a Teflon thread (GLIDE dental floss, W. L. GORE & ASSOCIATES Inc.). The hollow mould 12 so produced, which has on both sides a through-slot 19, 20 having a width of about 2 mm, is placed with the slot 19 facing downwards on the cellulose surface supported by the net 31 and cultivated at 28° C. in an incubator. It generally takes from 2 to 3 weeks for the hollow mould 12 to become populated with the bacteria and filled completely with cellulose. During this time it must be ensured that medium 27 that has been consumed or has evaporated is replaced, if necessary. When the hollow mould 12 is filled completely with cellulose, it can be opened and the cellulose hollow body 6, with the mould core 7, can be removed and heated in boiling-hot water. The wax thereby melts and the steel leaf 11 can be withdrawn without damaging the protuberances 3, 4. Wax residues that remain can easily be removed by rinsing with hot water (in the flow-through direction 6). The cellulose hollow body 6 can also be disinfected thereby.

The invention claimed is:

1. An elongate hollow body comprising crystalline cellulose, the hollow body having on an inside wall a plurality of protuberances which extend into a lumen of the hollow body, wherein the elongate hollow body and the protuberances are formed as a single piece.

2. The elongate hollow body according to claim 1, wherein the protuberances are in such a form that they are able to slow down the flow of a medium that is conveyed through the elongate hollow body to a greater extent in a shut-off direction than in a flow direction contrary to the shut-off direction.

3. The elongate hollow body according to claim 2, wherein the protuberances are in such a form that they can substantially suppress the flow of the medium in the shut-off direction.

4. The elongate hollow body according to claim 1, wherein the protuberances are in the form of pockets.

5. The elongate hollow body according to claim 4, wherein openings of the pockets point substantially to the same end of the elongate hollow body.

6. The elongate hollow body according to claim 4, wherein a plurality of protuberances are located opposite one another in the lumen of the hollow body at the same height with respect to the longitudinal direction of the hollow body.

* * * * *